Figure 1:
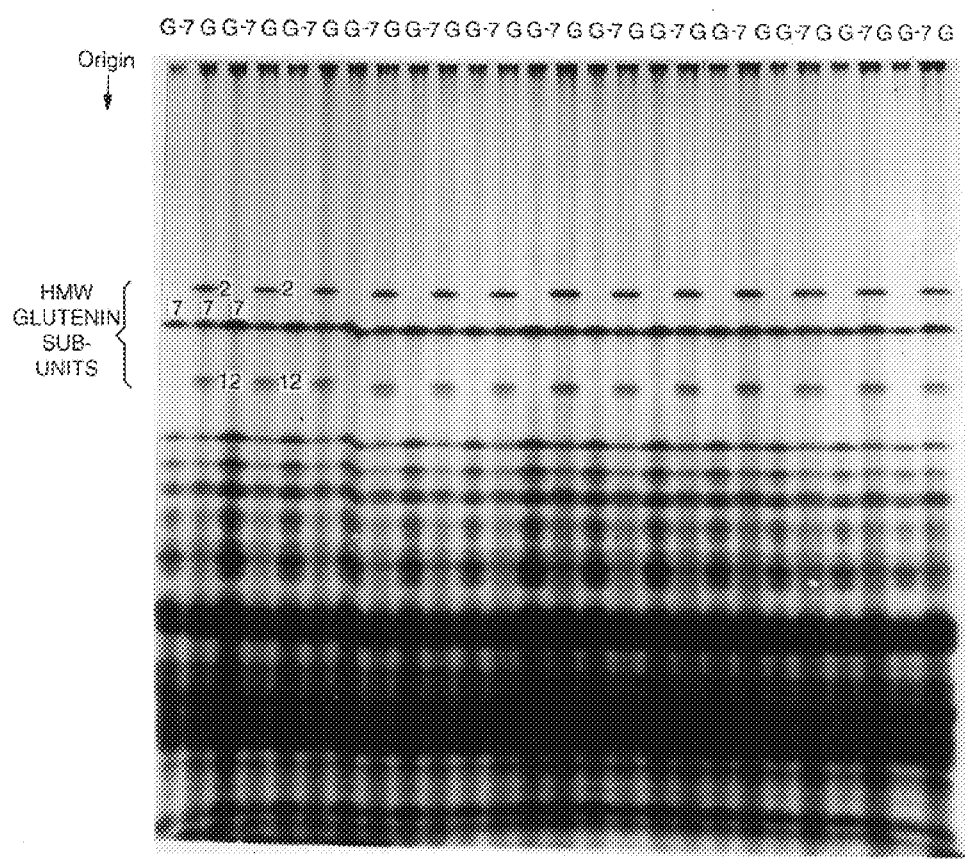

United States Patent [19]

Payne

[11] Patent Number: 5,859,315
[45] Date of Patent: Jan. 12, 1999

[54] SOFT-MILLING WHEATS WHICH PRODUCE DOUGH WITH LOW ELASTICITY

[75] Inventor: Peter Ivor Payne, Cambridge, United Kingdom

[73] Assignee: Unilever Patent Holdings BV, Netherlands

[21] Appl. No.: 735,986

[22] Filed: Oct. 25, 1996

Related U.S. Application Data

[62] Division of Ser. No. 384,794, Feb. 6, 1995, which is a continuation of Ser. No. 920,437, Oct. 19, 1992, abandoned.

[30] Foreign Application Priority Data

Feb. 19, 1990 [GB] United Kingdom ................. 90003740

[51] Int. Cl.$^6$ ...................................................... A01H 5/00

[52] U.S. Cl. ................................... 800/200; 800/DIG. 52; 800/DIG. 70; 800/250

[58] Field of Search ............................ 800/200, DIG. 52, 800/DIG. 58, DIG. 70, 250; 530/374, 375; 47/DIG. 58

*Primary Examiner*—Douglas W. Robinson
*Assistant Examiner*—Melissa L. Kimball
*Attorney, Agent, or Firm*—Cushman Darby & Cushman, IP Group of Pillsbury Madison & Sutro

[57] ABSTRACT

A soft-milling wheat which produces dough having exceptionally low visco-elasticity is provided by breeding from a variety having Glu-D1 double null trait, such as the landrace "Nap Hal". The wheat can be used in the manufacture of biscuits and wafers without the need to treat the flour with agents such as sodium metabisulphite.

1 Claim, 4 Drawing Sheets

SOFT-MILLING WHEATS WHICH PRODUCE DOUGH WITH LOW ELASTICITY

This is a division of application Ser. No. 08/384,794, filed Feb. 6, 1995 which was a continuation of Ser. No. 07/920,437, filed Oct. 19, 1992, now abandoned.

This invention relates to plants and to products derived therefrom.

When the grain of bread wheat (*Triticum aestivum*) is milled to a flour and mixed with water to form a dough, it develops unique viscoelastic properties. Viscoelasticity is a balance between two opposite forces, extensibility (viscous flow) and elasticity, and this balance varies significantly between wheat varieties. Viscoelasticity is primarily genetically controlled although it is affected to a small extent by growing conditions. The viscoelastic properties of a dough, and the milling properties of the grain, primarily determine the types of food that can be produced from a wheat. Wheat is used to make bread (leavened, non-leavened, flat, round or steamed), biscuits/cookies, noodles, breakfast cereals, wafers, and batters (either for food preparations, e.g. crumpets, pancakes, or as binding agents). The ratio of elasticity to extensibility needs to be high for leavened bread, intermediate for noodles and flat breads such as chapatis, and very low for wafers and semi-sweet biscuits. A bread dough has to be extensible to allow it to expand during fermentation at the proving stage of bread-making. As expansion occurs however, elastic forces must come into play so that, at optimal dough volume, expansion forces are counterbalanced by contraction (elastic) forces and these forces must be maintained until the starch gelatinises in the oven to form bread.

Wheat breeders usually differentiate wheat lines into hard-milling varieties and soft-milling varieties.

In a hard-milling wheat, there is strong adhesion between the protein and starch in the cells of the endosperm. Milling of the grain requires a lot of energy, and the starch granules suffer extensive damage. The flour can absorb a large amount of water during dough formation, and a final product made from the dough will normally have a relatively high moisture content. Hard-milling varieties are preferred for bread making, because the high moisture content delays the onset of staleness.

In a soft-milling wheat, adhesion between the protein and starch is weaker. Relatively little damage is caused to the starch during milling, and doughs of lower moisture content are formed. In the manufacture of dry products such as biscuits a soft-milling wheat is preferred, because less energy is needed to remove moisture during baking.

No wheat varieties are yet available commercially which are soft milling and from which a dough with low or very low elasticity can be prepared without either chemical treatment or the use of carefully controlled conditions (e.g. low temperature) during the preparation of the dough. The need to maintain critical conditions during dough preparation is obviously a serious constraint on manufacture. The need for chemical pre-treatment of the flour, usually conducted with sodium metabisulphite (SMS) would be avoided if possible, especially in view of current consumer pressure for foodstuffs that have not been "chemically treated". It is generally recognised that the biscuit-making industry would avoid the use of SMS if there was any commercially viable alternative.

There is a clear need for a soft milling wheat capable of providing a flour from which a highly extensible dough can be prepared at ambient temperature without the need for chemical or enzymic pre-treatment of the flour.

The viscoelasticity that develops in wheat doughs is primarily a function of the protein from the endosperm, called gluten, which usually comprises between 8% and 15% of the dry weight of wheat flour. The biochemistry and genetics of gluten have been extensively researched, with a view to improving the bread-making quality of wheat. It is now generally recognised that high-molecular-weight (HMW) subunits of glutenin, which make up only about 6–10% of the gluten content of wheat, are the key components in conferring elasticity and dough mixing stability. These HMW subunits are coded by three homoeoallelic loci in bread-wheat, called Glu-A1, Glu-B1 and Glu-D1, and are located on the long arms of chromosomes 1A, 1B and 1D respectively. Each locus contains two genes, called "x" and "y", so in principle wheat could have six different HMW glutenin subunits. However, the "y" gene at Glu-A1 is present but non-functional in all known commercially-cultivated wheats, so the maximum number of different subunits is five. Also, in some wheats, the "y" gene at Glu-B1 and the "x" gene at Glu-A1 are independently non-functional, so the minimum number of HMW glutenin subunits in any presently-available commercial wheat is three.

An experiment which indicated that HMW glutenin subunits confer elasticity to doughs was described by Lawrence, MacRitchie and Wrigley, *Journal of Cereal Science*, vol. 7, pages 109–112 (1988). They made use of one of the genotypes that comprise the primitive landrace from India called "Nap Hal". Samples of "Nap Hal" are freely available from several public germplasm collections, and have been so available since well before the filing date (19 Feb. 1990) of GB patent application No. 9003740.9 (Unilever PLC) from which we claim priority. For example, it is available under Accession No. 1362 from the AFRC Institute of Plant Science Research, Norwich, UK. Because "Nap Hall" is a landrace, it is genetically mixed and it is therefore necessary to purify the sample to homogeneity by selection, eg. using SDS-PAGE techniques on half-grains.

Approximately 20% of the grains that comprise "Nap Hal" are extremely unusual in lacking two go subunits coded by the "x" and "y" genes of Glu-D1, which we shall refer to herein as the "Glu-D1 double null" trait.

By repetitively backcrossing the "Nap Hal" line to the Australian bread-quality hard-milling variety "Gabo", which possesses five HMW glutenin subunits, Lawrence et al were able to produce sister lines genetically very similar to "Gabo" but varying in the number of HMW subunits. The line containing five HMW subunits had strong dough elasticity and good bread-making quality, like "Gabo". In contrast, the line with the Glu-D1 double null combined with a non-functional Glu-A1 "x" gene, giving it a total of only two HMW subunits, had minimal dough elasticity and very poor bread-making quality. Because such genetic lines containing the Glu-D1 double null have very poor bread-making quality, none has been knowingly introduced into wheat breeding programmes or released as commercial material. Furthermore, there has been no suggestion in the scientific literature of any potential advantages of the Glu-D1 double null trait if inserted into wheat genotypes that are not used in bread-making but are processed into other wheat-based foods.

The invention provides a soft-milling wheat genotype containing the Glu-D1 double null trait. This may be in the form of one or more stable true-breeding lines, or as more diverse material all of which exhibits the Glu-D1 double null trait and which can be used to introduce this trait into a breeding program.

The invention therefore provides soft-milling wheat from which flour giving highly extensible doughs with low or very low levels of elasticity, depending on the genotype, can be prepared. This range of elasticity is much lower than the range of elasticity currently observed in doughs from commercial soft-milling wheat. The wheat of the invention greatly facilitates the production of semi-sweet biscuits, non-fermented crackers, wafers, and food or food ingredients made from batters, which are made from soft-milling wheats because low water absorption by the flour is required.

In one aspect, the invention provides soft-milling wheat having an SDS-sedimentation volume, measured as described below in Experiment 2 and corrected to 11% protein, of not greater than about 30 ml, preferably not greater than about 25 ml, and more preferably not greater than about 20 ml.

A soft-milling wheat in accordance with the invention, with the above novel properties, can be obtained for example by transferring the Glu-D1 double null trait, eg. from "Nap Hall" or from a "Nap Hal" derivative which is hard-milling, by repetitively backcrossing into a soft-milling wheat, such as "Galahad", and selecting half grains at each generation, eg. by SDS-PAGE analysis.

The viscoelastic properties of a wheat in accordance with the invention will be determined primarily by the number of different HMW glutenin subunits it contains. The possibilities are shown in the Table below.

TABLE

Possible HMW glutenin subunit combinations of genotypes in accordance with the invention

|   | Glu-A1 "x" | Glu-B1 "x" | Glu-B1 "y" | Glu-D1 "x + y" | Subunit No. |
|---|---|---|---|---|---|
| 1 | + | + | + | − | 3 |
| 2 | − | + | + | − | 2 |
| 3 | − | + | − | − | 1 |
| 4 | − | − | + | − | 1 |
| 5* | − | + | − | − | 1 |
| 6* | − | − | + | − | 1 |

The genotypes in the Table have been arranged approximately with decreasing orders of elasticity expected in their doughs. Genotypes 5 and 6 have identical HMW subunit compositions to genotypes 3 and 4 respectively, except that they contain the 1 BL/1 RS chromosome that occurs in many high-yielding feed/biscuit wheats (L=long arm, S=short arm). They provide less-elastic doughs than their counterparts because chromosome 1 RS (derived from rye) contains the Gli-R1 locus instead of the Gli-B1 on 1BS, present in most wheats. Gli-B1 contains a family of genes coding for low-molecular-weight (LMW) subunits of glutenin, whereas Gli-R1 does not. This reduces even further the amount of elastic glutenin in doughs and batters.

More particularly, the invention provides a soft milling wheat capable of providing a flour from which a dough can be prepared at ambient temperature and is sufficiently inelastic to enable crisp farinaceous edible products such as biscuits, for example semi-sweet biscuits, and non-fermented crackers, to be manufactured therefrom without pretreatment of the flour with SMS.

The invention also encompasses soft non-chemically-treated wheat flour from which a dough with low or very low elasticity can be prepared at ambient temperature.

More particularly, the invention provides soft wheat flour that does not require treatment with SMS to make a dough at ambient temperature that is sufficiently inelastic for the manufacture of crisp farinaceous edible products such as biscuits and the like.

An important embodiment of the invention is soft wheat flour that enables the production of a dough that is sufficiently non-elastic to allow crackers to be manufactured without the need for treatment of the flour with SMS or proteolytic enzymes.

A further embodiment is a soft wheat in which the grain protein is sufficiently soluble for gluten not to develop significantly in batter made from the wheat. This is particularly important in wafer manufacture.

The invention also encompasses dough prepared from flour as defined in the preceding paragraphs, and to edible products made by cooking such a dough.

The rheological properties (eg. elasticity and elastic stability) of doughs can be characterised by several types of apparatus. The Brabender Farinograph can be used to estimate the maximum degree of elasticity that can be tolerated to make semi-sweet biscuits without SMS treatment. The Farinograph should be calibrated using white flour (protein content between 10 and 11.5%) of a commonly grown bread-quality, hard milling wheat. For example, the UK variety "Mercia" can be used, to give a band width of 80 Brabender Units at peak viscosity when peak viscosity is adjusted to the 600 Brabender Unit line. At this calibration, a genotype embodying the present invention and suitable for making semi-sweet biscuits will have a band thickness five minutes after reaching peak viscosity of less than 20 Brabender Units. In addition, the Degree of Softening of the dough, ie. the difference in viscosity at peak and five minutes of mixing after reaching peak, should be at least 250, and preferably at least 300, Brabender Units, compared to that of 95 Brabender Units for Mercia.

In referring to the preparation of dough at ambient temperature, we mean that a dough having satisfactory inelastic properties can be prepared directly from the non-chemically treated flour at typical temperate climate factory temperatures, which will generally be at least 20° C.

With the present invention the number of different HMW subunits in wheat can be reduced to two or one, depending on the genotype.

A particular aspect of the invention is a soft milling wheat flour in which the number of different HMW glutenin subunits is below 3, and the percentage of high molecular weight (HMW) subunits in glutenin is in the range of about 2 to about 6%.

The benefits of the present invention are achieved by providing a soft milling wheat in which a Glu-D1 double null is present. The invention encompasses soft-milling wheat having this essential genetic characteristic. The invention also encompasses the use of a wheat line exhibiting the Glu-D1 double null trait in the production, eg. by breeding or genetic engineering, of soft-milling wheat.

A particular strain of semi-dwarf, red-grained, soft-milling winter wheat having this essential characteristic, designated "Galahad-7", has been deposited, in accordance with the provisions of the Budapest Treaty, in the National Collections of Industrial and Marine Bacteria, Aberdeen, Scotland under Accession No. NCIMB 40251, on 19 Jan. 1990. The deposited sample, which exhibits residual genetic variation, does not constitute seed that would be regarded as a true registerable plant variety. Nevertheless, the sample is true-breeding with regard to the Glu-D1 double null trait.

The invention encompasses soft-milling wheat having the essential genetic characteristics, in terms of dough properties, exhibited by strain NCIMB 40251, and also the use of this strain in the production, eg. by breeding or genetic engineering, of soft-milling wheat.

For a wheat to exhibit the Glu-D1 double null trait, each of the "x" and "y" genes at Glu-D1 should be either inactive or absent. Generally, both will be absent.

A further embodiment of the invention involves the production of a strain of wheat, involving the steps of:
a) selecting a hard-milling wheat strain possessing the Glu-D1 double null trait;
b) crossing the hard-milling strain with a soft-milling wheat strain which naturally produces relatively elastic dough;
c) back-crossing the resulting strain into a soft-milling wheat strain;
d) selecting grains exhibiting the Glu-D1 double null trait at half the normal gene dosage, by analysis of embryo-less half grains, the corresponding half-grains being retained for germination;
e) germinating the corresponding half-grain of the selected soft-milling Glu-D1 double null strain, and conducting a further back-crossing and half-grain analysis for the Glu-D1 double null trait;
f) germinating the corresponding half-grains from step (e), and growing and allowing to self-pollinate grains containing the Glu-D1 double null trait in the homozygous state; and
g) determining which of the resulting lines homozygous for the Glu-D1 double null trait are soft-milling.

Semi-sweet biscuits are made from thin sheets of dough. Any elasticity present would cause the dough to contract when released from the rollers, ruining biscuit shape and pattern, and making biscuits difficult to stack and probably causing the biscuits to have a greater than desired hardness. At least two approaches can be taken at the factory. The reducing agent SMS is added in those countries where it is permitted. This breaks down the disulphide bonds in glutenin and non-elastic glutenin subunits are released. The use of SMS is under review in those countries where it is still allowed to be used, in line with current trends in reducing food additives. An alternative approach is to manufacture at low temperatures so that the extensible component of gluten preferentially develops in the dough. Another alternative is to overmix the dough prior to sheeting. Both these processes are expensive. These difficulties will be minimised if a soft-milling wheat is used of the type made possible by this invention with one HMW glutenin subunit.

The effect of reducing the number (and hence proportion) of HMW glutenin subunits in gluten is to reduce the mean molecular weight of glutenin, see Payne and Corfield, *Planta*, Vol. 145, pages 83–88 (1979). This increases the rate at which gluten hydrates when water is added to flour, and also greatly increases the solubility of gluten, as seen in Experiment 3 below. This is advantageous in the making of semi-sweet biscuits because the flour will form a dough with less water than conventional varieties (when SMS is not used) even in the presence of sugar and fat. Consequently, much less water will have to be driven from biscuits when they are baked, so greatly increasing biscuit throughput and reducing costs.

Crackers that are not fermented, such as "Ritz"-type crackers, also require a non-elastic dough for their manufacture. SMS is sometimes used, but more often an enzyme inoculation containing one or more proteases is added to remove elasticity. This step has to be very carefully controlled to achieve maximum hydrolysis of glutenin while avoiding significant damage to other, functional components; a hold-up in the factory processing line would be disastrous. Wheat varieties developed with the current invention do not require the addition of proteases or SMS.

Wafers are made from batters rather than from doughs and a major problem in their manufacture is that the batters have to be pumped through tubes from the site of flour-water mixing, and then through finer nozzles to the site of wafer formation. There is a tendency, using currently available wheat varieties, for gluten to develop and then solidify in the batters during such transit, causing blockage in the tubes and significant delays in manufacture. This is particularly the case where sugar is not included in the batter formulation.

The chances of gluten development occurring during transit are clearly much greater if the ratio of flour to water in batters is raised. But there is another variable that relates to the mean molecular size of glutenin. In commercial wheat varieties, gluten development is accelerated by the long glutenin molecules becoming tangled with themselves and with other gluten molecules. In genotypes embodying the invention, the glutenin molecules tend to be much shorter, so molecular entanglement is much reduced. Also, the viscosity of such batters is less than the viscosity of batters made from conventional varieties because of the decrease in molecular size of the large glutenin molecules. For these reasons, therefore, not only will blockages in transit tubes not occur with wheat embodying the invention, but thicker batters can be prepared and manipulated, thus creating new possibilities in the production of high-density wafers.

Pancakes and crumpets are also made from batters, as also are food binders (for instance the agent that binds bread crumbs to fish products). Gluten development can occur in conventional batter and result in a "lumpy" product. The use of wheat embodying the present invention will avoid this problem.

A soft-milling wheat of the invention can be grown, harvested and milled to produce flour in the normal way. The resulting flour can be converted to dough or batter using conventional techniques and equipment, although of course the need to pre-treat the flour with SMS or other agents to reduce the dough elasticity can be avoided. The dough or batter can be made into cooked products such as biscuits, crackers or wafers in the normal way. If desired, a soft-milling wheat of the invention can be blended with other soft-milling wheat, or hard-milling wheat, either before or after milling, to decrease the dough strength of the blend.

Wheat in accordance with the invention can be produced by the following procedure, which is given here by way of example only.

EXAMPLE

A commonly grown soft wheat, variety "Galahad", was crossed with a "Sicco" line containing the "Nap Hall" Glu-D1 double null ("Nap Hal"x"Sicco"$^5$). "Galahad" contains 3 HMW subunits, namely subunit 7 coded by the "x" gene of Glu-B1 and subunits 2 and 12 coded by the "x" and "y" genes respectively of Glu-D1. The "y" gene of Glu-B1 and the "x" and "y" genes of Glu-A1 are non-functional. The $F_1$ generation was backcrossed to "Galahad", and embryo-less half grains analysed by means of SDS-PAGE. About half the grains had weak bands of subunits 2 and 12 (encoded by the Glu-D1 locus from "Galahad"), as opposed to strong bands, and these alone were germinated and the adult plants backcrossed again to "Galahad". Embryo-less half grains were again analysed by SDS-PAGE and those with weak bands corresponding to subunits 2 and 12 were selected and germinated. The mature plants were allowed to self pollinate, and those grains that completely lacked subunits 2 and 12 (about 25% of the total) were selected, and the corresponding half-grains germinated in a cold glasshouse to produce a large stock of selfed seed. This line, as shown in FIG. 1, contained only one HMW glutenin subunit, subunit 7 that is coded at by the "x" gene Glu-B1 and inherited from "Galahad". This line was designated "Galahad-7", and is the strain deposited as NCIMB 40251. FIG. 1 of the accompanying drawings depicts SDS-PAGE analysis of seed proteins from "Galahad" (G) and "Galahad-7" (G-7).

The following experiments demonstrate that doughs made from "Galahad-7", a line containing the Glu-D1 double null and only one HMW glutenin subunit, are very extensible and very poorly elastic. They also demonstrate its greater suitability for manufacture into semi-sweet biscuits and wafers, than conventional varieties.

Experiment 1

Figure 2:
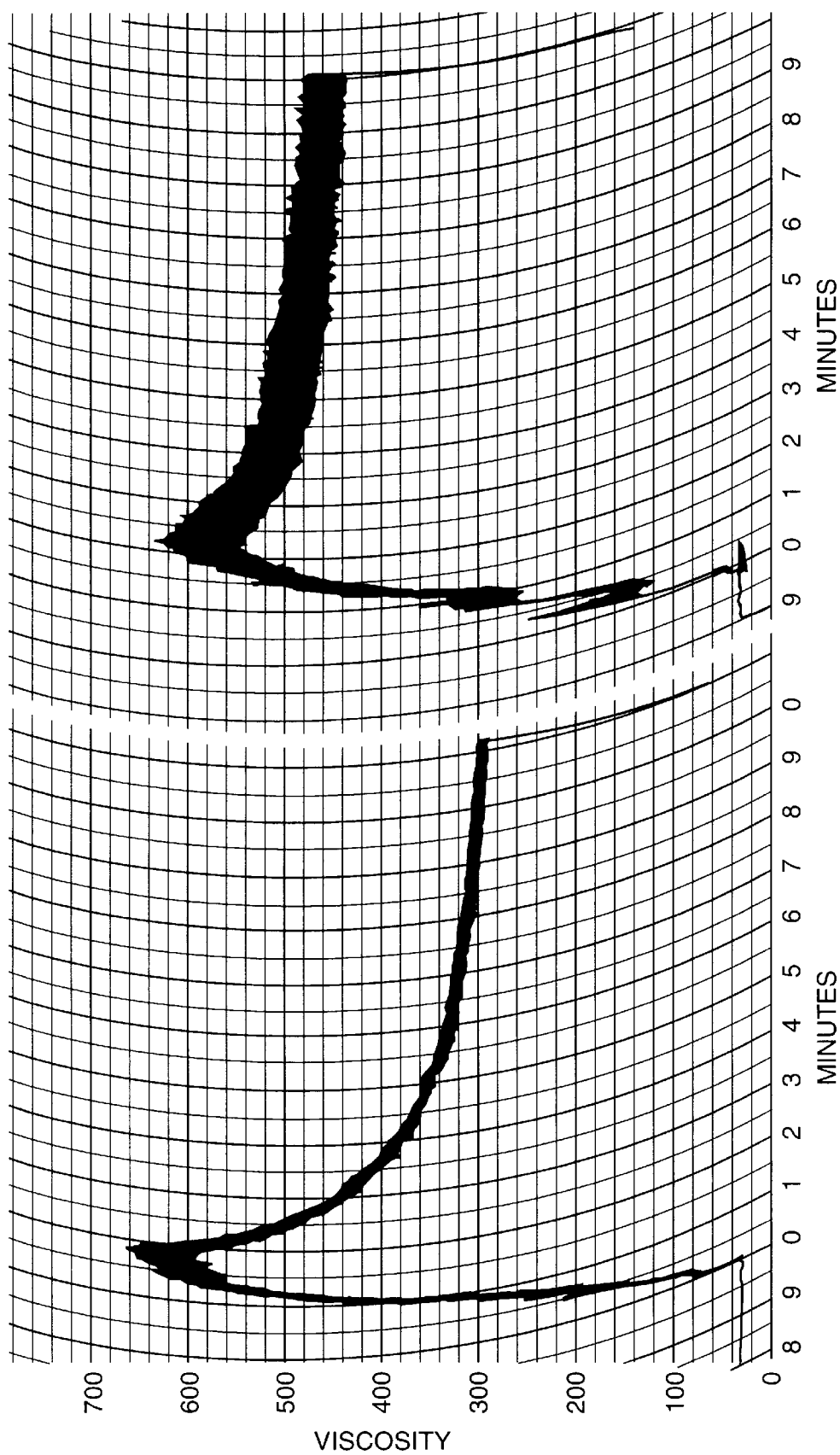

FIG. 2 of the accompanying drawings shows Farinograph traces of "Galahad-7" (G-7) and "Galahad" (G).

The rheological properties of dough made from "Galahad" and "Galahad-7" flours were studied using the Brabender Farinograph. The apparatus was first calibrated with dough made from white flour (protein content between 10.0 and 11.5%) of "Mercia", a hard milling variety widely grown in the UK for the bread baking industry. Using the International Association for Cereal Chemistry (ICC) method No. 115 and the 300g mixing bowl, the Farinograph trace was adjusted to give a band thickness of 80 Brabender Units at peak viscosity on the 600 Brabender Unit line.

The Degree of Softening determined by the Farinograph is the difference in viscosity at peak and after mixing for a further five minutes. The value for "Galahad" was 110 Brabender Units, greater than expected for a strong mixing bread quality wheat, but slightly less than that for a typical biscuits/feed wheat. By contrast the Degree of Softening for "Galahad-7" dough was much greater, at 300 Brabender Units.

The band thickness of the trace of "Galahad" after five minutes of mixing beyond peak viscosity was 55 Brabender Units.

By contrast the corresponding thickness of the trace of "Galahad-7" was only 15 Brabender Units, showing that its dough had only a minute fraction of the elasticity present in "Galahad" dough. To the best of our knowledge no Farinograph patterns have been published for wheat that demonstrate such a high degree of softening and such a low level of elasticity, except when a reducing agent such as sodium metabisulphite had been added to the dough.

Experiment 2

The SDS(sodium dodecyl sulphate)-sedimentation test, described by Axford, McDermott and Redman, *Cereal Chemistry*, vol. 56, pages 582–584 (1979), measures the volume of sediment after mixing wholemeal flour in a lactic acid, SDS solution under controlled conditions and then allowing to settle for a specified period. The larger glutenin molecules which are primarily responsible for elasticity and dough strength form a gel and increase the volume of the sediment. The protein molecules imparting extensibility dissolve. The method is used extensively in wheat breeding programmes to select for bread-making quality (large sedimentation volumes) and at wheat mills as a quick test for bread quality prior to accepting a grain load. The SDS volume of the "Galahad-7" (6.0 g flour at 15% w/v water content) sample was 22 ml (protein content=14.2%), that of "Galahad" was 51 ml (10.2% protein). By contrast the volume of "Apostle", a good bread-quality wheat, was 85 ml at about 10.5% protein.

The SDS-sedimentation volumes of varieties grown in a replicated field trial in Cambridgeshire, and harvested in the summer of 1990, were compared with the sedimentation volume of "Galahad-7" grown at Cambridge in the same season. The varieties are representative of the three major wheat categories grown commercially in the UK: (1) hard milling wheat of good bread-making quality; (2) hard milling feed wheat, and (3) soft milling wheat suitable for feed and biscuits. The SDS-sedimentation volume of "Galahad-7" was very much smaller than those of all the other varieties tested, because it contains much less gel protein. Gel protein consists primarily of long elastic glutenin molecules.

| Variety | Mean SDS volume (ml) | Mean SDS volume (ml) corrected to 11% protein |
|---|---|---|
| Hard-milling, bread-quality varieties | | |
| Mercia | 70 | 67 |
| Apostle | 78 | 75 |
| Hereward | 79 | 77 |
| Dean | 57 | 56 |
| Pastiche | 93 | 81 |
| Torfrida | 91 | 88 |
| CWW 88/6 | 72 | 73 |
| CWW 89/3 | 87 | 84 |
| CWW 89/4 | 72 | 69 |
| CWW 89/5 | 93 | 89 |
| CWW 90/3 | 91 | 88 |
| CWW 90/4 | 75 | 72 |
| mean | 80 | 77 |
| Hard-milling, feed wheats | | |
| Slejpner | 49 | 49 |
| Haven | 42 | 43 |
| CWW 89/2 | 54 | 50 |
| CWW 89/7 | 53 | 51 |
| CWW 90/5 | 50 | 48 |
| CWW 90/6 | 54 | 51 |
| CWW 90/7 | 55 | 52 |
| | 51 | 49 |
| Soft-milling, biscuit/feed wheats | | |
| Galahad | 52 | 51 |
| Apollo | 45 | 45 |
| Riband | 52 | 55 |
| Beaver | 43 | 44 |
| Tara | 33 | 34 |
| CWW 89/6 | 49 | 50 |
| CWW 90/2 | 41 | 39 |
| | 45 | 45 |
| Genotype with the Glu-D1 null | | |
| Galahad-7 | 18 | 17 |

The coded (unnamed) varieties were currently being assessed in the UK National List Trials. A linear, direct relationship was assumed between SDS sedimentation volume and protein content. The results presented are the mean of three determinations. The largest difference in the SDS volumes of replicate determinations was 7.0 ml (for CWW 89/7), but the mean difference for all varieties was only 1.4 ml.

Experiment 3

Figure 3:
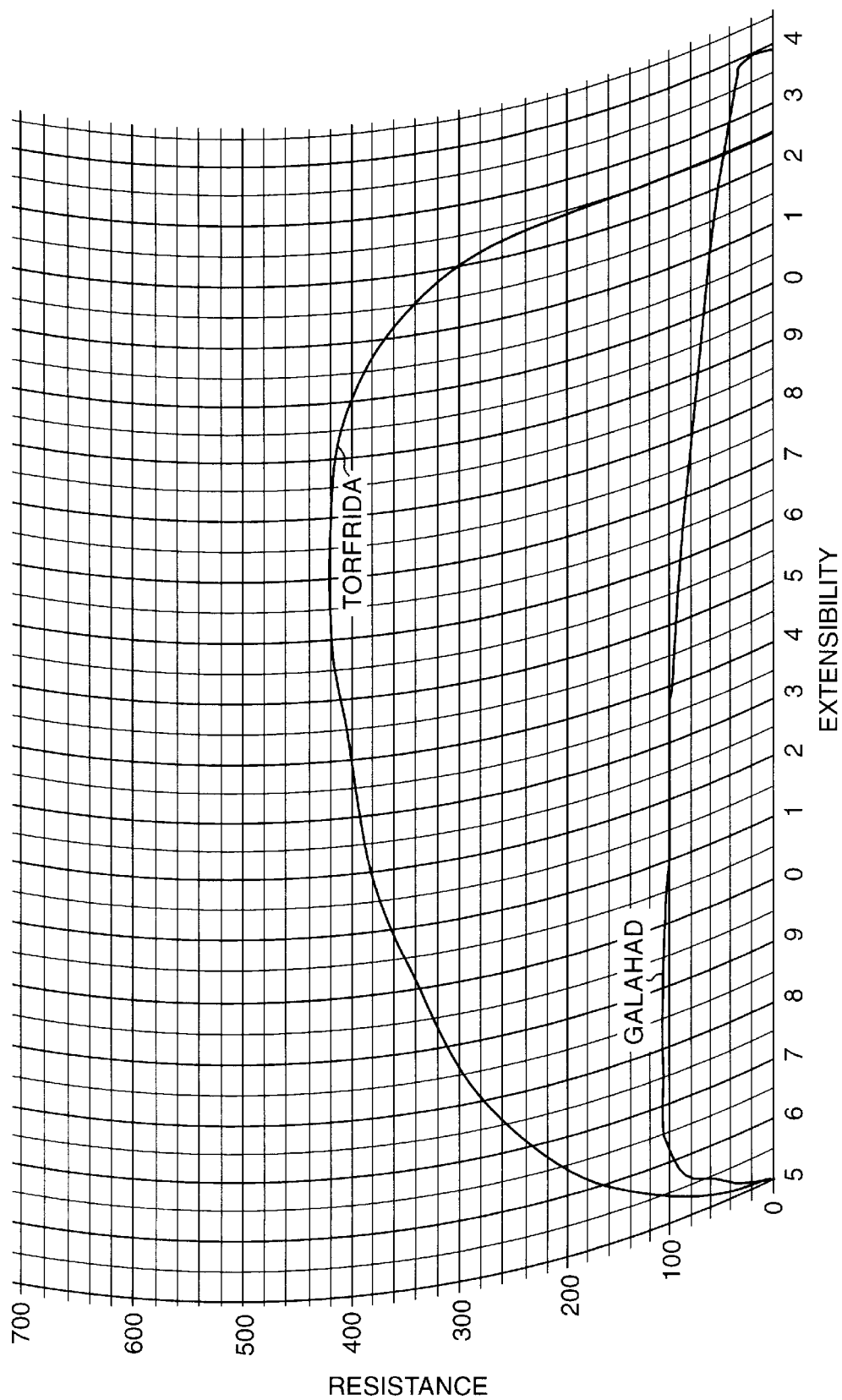
Figure 4:
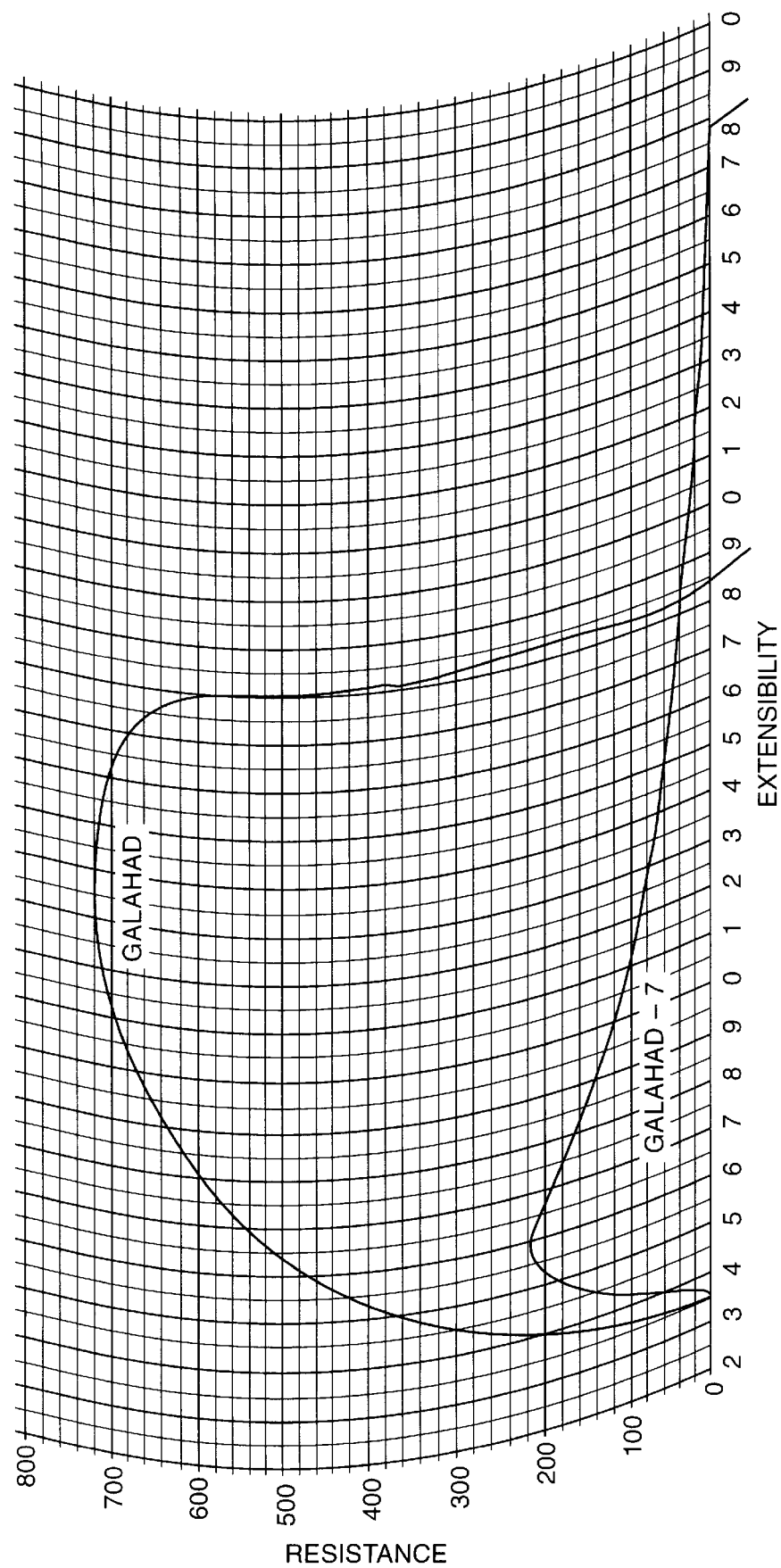

FIG. 3 of the accompanying drawings shows standard Extensograph traces of "Torfrida" and "Galahad", and FIG. 4, traces of "Galahad" and "Galahad-7" whose doughs were made with increased amounts of salt in them.

The viscoelastic properties of the doughs of "Galahad" and "Galahad-7" were compared using the Brabender Extensograph. This instrument measures both the resistance of the dough piece to stretching (its elasticity) and the distance the dough can be stretched before it breaks into two pieces (its extensibility). Dough of "Torfrida" is both elastic and extensible, and suitable for bread-making whereas that of the biscuit wheat "Galahad" is much less elastic. Dough of "Galahad-7" is so fluid and sticky when prepared by the ICC Standard method no. 114, it could not be tested satisfactorily. Accordingly a new method was developed by mixing flour with an increased amount of salt (18 g per 300 g flour instead of 6 g per 300 g) and adjusting mixing viscosity to the 800 Brabender Unit line of the Farinograph instead of the 500 line. Additionally the resting period in the Farinograph bowl between mixes was reduced from 5 to 4 minutes and the resting period in the Extensograph prior to stretching, from 45 to 20. The dough of "Galahad" now showed appreciable resistance to stretching, but when dough of "Galahad-7" was similarly prepared it became handleable for the first time yet remained virtually devoid of elasticity, while being extremely extensible.

Experiment 4

This experiment demonstrates that relatively little water is required to form a dough with "Galahad-7", a very important positive property for making semi-sweet biscuits.

Water was slowly added to 50 g of "Galahad-7" flour with hand kneading. When close to dough formation, single-ml aliquots of water were added. A stiff but very extensible dough was achieved after the addition of 23 ml of water. Under similar conditions, 50 g of "Galahad" flour required 28 ml and then a much tougher, elastic dough was formed.

A second experiment was carried out in which water was replaced by a 2.5% (w/v) salt solution. Fifty grams of "Galahad-7" flour required 25 ml to make a very extensible dough but the same weight of "Galahad" required 30 ml to make a much more elastic dough.

In further experiments in which a biscuit formulation was used (8 g biscuit oil, 10.5 g sugar, 0.17 g salt and 1.25 g skimmed milk powder/50 g flour) similar results were obtained. The "Galahad-7" mixture required 21.3 ml of water at room temperature whereas the "Galahad" mixture required 23.0 ml. After a short period of hand kneading, "Galahad-7" dough became free flowing but that of "Galahad" remained tough and elastic, even after prolonged kneading.

The experiments described so far demonstrate that "Galahad-7" presents a new type of wheat, being more easily hydratable than conventional wheats, having much lower SDS-sedimentation volumes and producing very weak and inelastic doughs that are very extensible. Its properties are primarily due to the lack of HMW glutenin subunits coded by the Glu-D1 locus.

Experiment 5

Samples of "Galahad-7" and "Galahad" were tested by the Flour Milling and Baking Research Association (FMBRA) using their small-scale test-baking procedure for semi-sweet biscuits, with and without SMS treatment. "Galahad" produced unacceptably hard biscuits when SMS treatment was omitted. "Galahad-7" however produced an acceptable biscuit with a softer texture both with and without SMS treatment. The thicknesses of the biscuits were also measured. The mean thickness of "Galahad-7" without SMS treatment was 6.0 mm, only 0.2 mm thicker than "Galahad" with SMS treatment. "Galahad" biscuits made without SMS treatment were much thicker, at 6.9 mm, because elastic components in the dough caused lengthwise contraction of the biscuits before baking. Two pilot-scale biscuit making tests were undertaken with "Galahad-7", one in the presence of sodium metabisulphite and the other without this reducing agent. The dough of the latter showed some residual elasticity and it produced biscuits that were slightly thicker (5.5 mm versus 4.8 mm) and heavier (6.8 g versus 6.2 g) than the control test with SMS. Nevertheless, the biscuits produced without SMS were judged to be soft textured and commercially acceptable. These results show that "Galahad-7" can be used to make satisfactory biscuits without the need for SMS treatment. Residual elasticity would have been reduced by a relatively small increase in mixing time/energy.

Experiment 6

Flour samples of "Galahad", "Galahad-7", and a typical commercial blend for biscuit-making, were tested at FMBRA for their suitability for processing into wafers, using the FMBRA Wafer Batter Mixing Test. 475 ml of water at 43° C. were placed in the bowl of a Kenwood Major mixer fitted with a whisk attachment. The mixer was switched on at the slow speed setting and 395 g flour was added within 30 seconds. The mixture was whisked further at the fastest speed for two minutes. Then, 200 g batter was immediately placed in a liquidiser attachment of the same mixer, and mixed at speed setting 3. During this time a trace from a chart recorder examined the power input via a power meter placed between the electricity supply and the mixer.

The biscuit and "Galahad" batters showed traces of gluten development during the whisking stage. Gluten continued to form during the liquidising stage and reached maximum development after 21.6 seconds for the biscuit-batter and 25.2 seconds for the "Galahad" batter. The gluten was completely broken down after a further two seconds for the biscuit batter and three seconds for the "Galahad" batter. There was no discernable gluten development in the "Galahad-7" batter during whisking, and a very quick formation (3.75 seconds) and destruction (3 seconds) of gluten during the liquidising stage. At the end of the experiment, the final viscosity of the batter was determined in a viscosity cup with a 7.75 mm diameter hole. It took 230 seconds and 302 seconds for 200 g batter to pass from the cup, for the biscuit blend and "Galahad" respectively. By contrast, "Galahad-7" batter was very thin and only took 59 seconds to pass from the viscosity cup.

Wafer sheets were made from 2.52 kg of "Galahad-7" and were shown to be of acceptable quality, similar to the wafer flour control.

These experiments show that batters from "Galahad-7" are most unlikely to cause blocking problems in commercial wafer production, and that there is considerable scope to develop new types of wafers from high density batters.

Experiment 7

This experiment demonstrates that the Glu-D1 double null trait is caused by the loss of the genes from this locus rather than the genes still being present but altered so they cannot function. DNA was extracted from leaves of (Nap Hal× Sicco[5]), the Glu-D1 double null donor parent of "Galahad-7", digested with the restriction enzyme SstI and fractionated by agarose gel electrophoresis. The fractionated DNA was transferred to a Zetaprobe nylon membrane and probed with the radioactive CDNA pTag 1290, which specifies part of the coding sequence of a HMW glutenin subunit gene. The probe hybridised with only three DNA bands, two derived from chromosome 1A and the other from 1B. The chromosome 1D band (ie. that containing the Glu-D1 locus) that is detected in all varieties, and which usually has a size of 4.8 Kb for this restriction enzyme, was absent.

I claim:

1. Wheat of strain NCIMB 40251.

* * * * *